(12) United States Patent
Lahiri et al.

(10) Patent No.: US 9,440,979 B2
(45) Date of Patent: Sep. 13, 2016

(54) PROCESS FOR THE PREPARATION OF PRALATREXATE

(71) Applicant: Fresenius Kabi Oncology Limited, New Delhi (IN)

(72) Inventors: Saswata Lahiri, Gurgaon (IN); Nitin Gupta, Gurgaon (IN); Hemant Kumar Singh, Gurgaon (IN); Nilendu Panda, Gurgaon (IN); Vishal Handa, Gurgaon (IN); Azim Abul, Gurgaon (IN); Chandan Kumar Gupta, Gurgaon (IN); Sunil Sanghani, Gurgaon (IN); Ghanashyam Madhukar Sonavane, Gurgaon (IN)

(73) Assignee: FRESENIUS KABI ONCOLOGY LIMITED, New Delhi (IN)

( * ) Notice: Subject to any disclaimer, the term of this patent is extended or adjusted under 35 U.S.C. 154(b) by 0 days.

(21) Appl. No.: 14/416,127

(22) PCT Filed: Jul. 18, 2013

(86) PCT No.: PCT/IB2013/055912
§ 371 (c)(1),
(2) Date: Jan. 21, 2015

(87) PCT Pub. No.: WO2014/016740
PCT Pub. Date: Jan. 30, 2014

(65) Prior Publication Data
US 2015/0183789 A1  Jul. 2, 2015

(30) Foreign Application Priority Data

Jul. 23, 2012  (IN) .......................... 2271/DEL/2012
Apr. 11, 2013  (IN) .......................... 1090/DEL/2013

(51) Int. Cl.
C07D 475/08 (2006.01)
C07C 67/343 (2006.01)

(52) U.S. Cl.
CPC ........... *C07D 475/08* (2013.01); *C07C 67/343* (2013.01)

(58) Field of Classification Search
CPC .................................................. C07D 475/08
See application file for complete search history.

(56) References Cited

U.S. PATENT DOCUMENTS

| 5,354,741 | A  | 10/1994 | Patel |
| 5,374,726 | A  | 12/1994 | DeGraw et al. |
| 6,028,071 | A  | 2/2000 | Sirotnak et al. |
| 2011/0190305 | A1 | 8/2011 | Pronk |

FOREIGN PATENT DOCUMENTS

| WO | 2011/096947 | 8/2011 |
| WO | 2013/096800 | 7/2013 |

OTHER PUBLICATIONS

DeGraw et al., "Synthesis and Antitumor Activity of 10-Propargyl-10-Deazaaminopterin," J. Med. Chem., 1993, 36, 2228-2231.

*Primary Examiner* — Bruck Kifle
(74) *Attorney, Agent, or Firm* — Occhiuti & Rohlicek LLP

(57) ABSTRACT

An improved process for the preparation of Pralatrexate which is less hazardous. The invention further relates to novel intermediates and process thereof useful for the preparation of Pralatrexate. The present invention also relates to a substantially pure Pralatrexate and a process for obtaining the same in high yield.

25 Claims, 1 Drawing Sheet

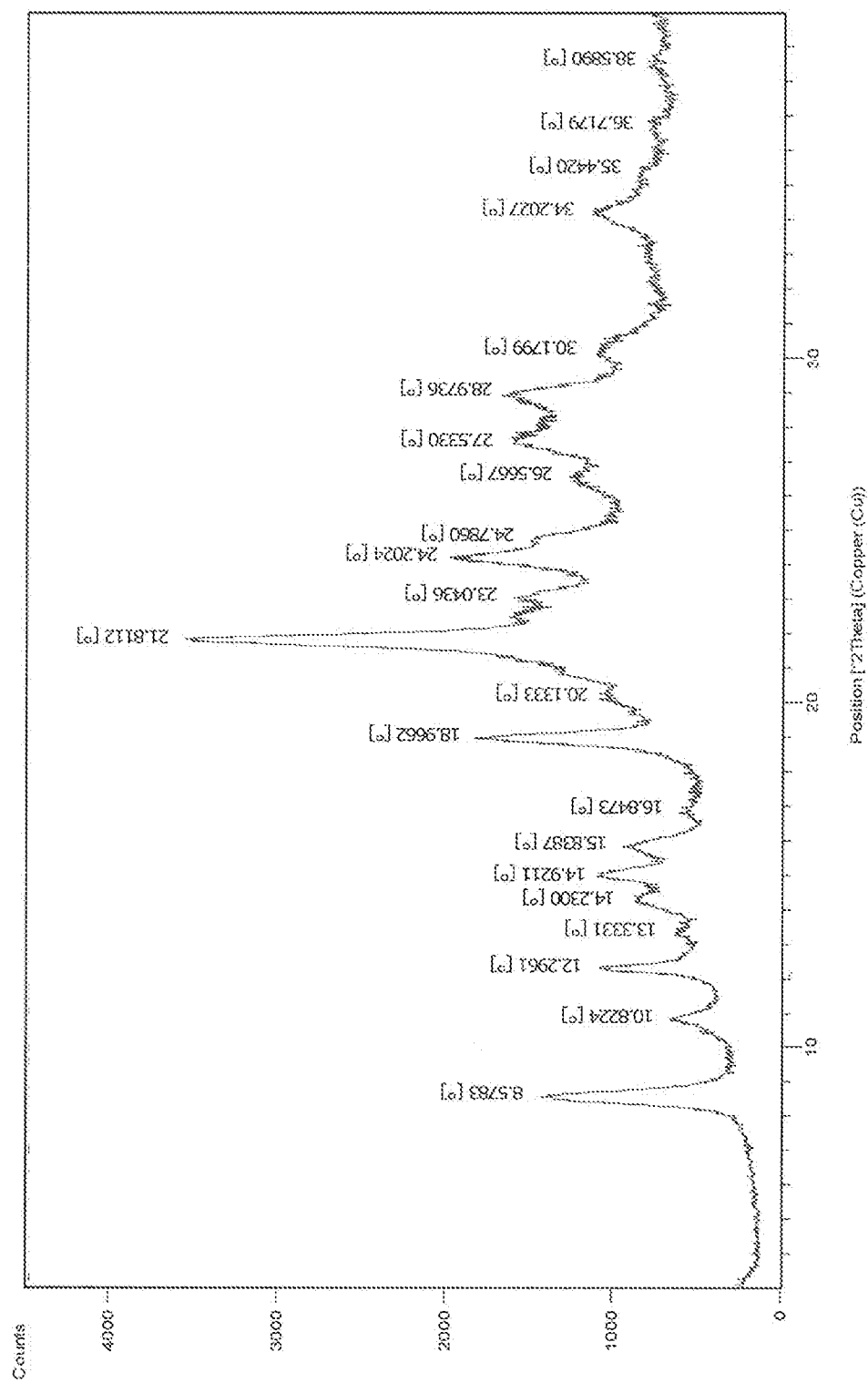

PROCESS FOR THE PREPARATION OF PRALATREXATE

CROSS REFERENCE TO RELATED APPLICATIONS

This application is a national stage application under 35 U.S.C. §371 of International Application No. PCT/IB2013/055912, filed on Jul. 18, 2013, which claims priority to Indian Application No. 2271/DEL/2012, filed on Jul. 23, 2012 and Indian Application No. 1090/DEL/2013, filed on Apr. 11, 2013, the contents of which are hereby incorporated by reference in their entirety.

FIELD OF THE INVENTION

The present invention relates to an improved process for the preparation of novel of Pralatrexate. The invention further relates to novel intermediates useful for the preparation of Pralatrexate. The present invention also relates to a substantially pure Pralatrexate and a process for obtaining the same.

BACKGROUND OF THE INVENTION

Pralatrexate, chemically known as "(2S)-2-[[4-[(1RS)-1-[(2,4-diaminopteridin-6-yl)methyl]but-3-ynyl]benzoyl]-amino]pentanedioic acid", also known as "10-Propargyl-10-deazaminopterin" or "PDX", is a compound which has been tested and found useful in the treatment of cancer. In its racemic form, 2S)-2-[[4-[(1RS)-1-[(2,4-diaminopteridin-6-yl)methyl]but-3-ynyl]benzoyl]amino]-pentanedioic acid has been approved by the U.S. Food and Drug Administration (FDA) as a treatment for relapsed and refractory peripheral T-cell lymphoma.

Pralatrexate, represented by Formula (I), was first disclosed in *Journal of Medicinal Chemistry.* 36: 2228-2231 (1993) by DeGraw et al., and subsequently in U.S. Pat. No. 5,374,726 and U.S. Pat. No. 5,354,741.

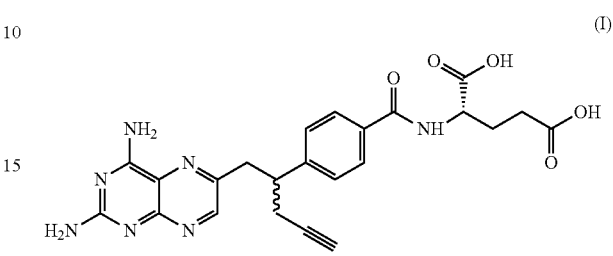

DeGraw et al., publication, U.S. Pat. No. 5,374,726 and U.S. Pat. No. 5,354,741 disclose method for the synthesis of Pralatrexate of Formula (I), comprising alkylation of homoterephthalic acid dimethyl ester with propargyl bromide using Potassium Hydride, which is further coupled with 2,4-diamino-6-bromomethylpteridine in presence of Potassium Hydride followed by hydrolysis in presence of NaOH in 2-methoxyethanol-water mixture and decarboxylation at high temperature in DMSO and subsequent coupling with L-glutamic acid diethyl ester using t-butyl chloroformate and a base, and finally hydrolysis of the product with NaOH in 2-methoxyethanol-water mixture to give Pralatrexate of Formula (I). The process is outlined below as synthetic Scheme-1.

Scheme-1

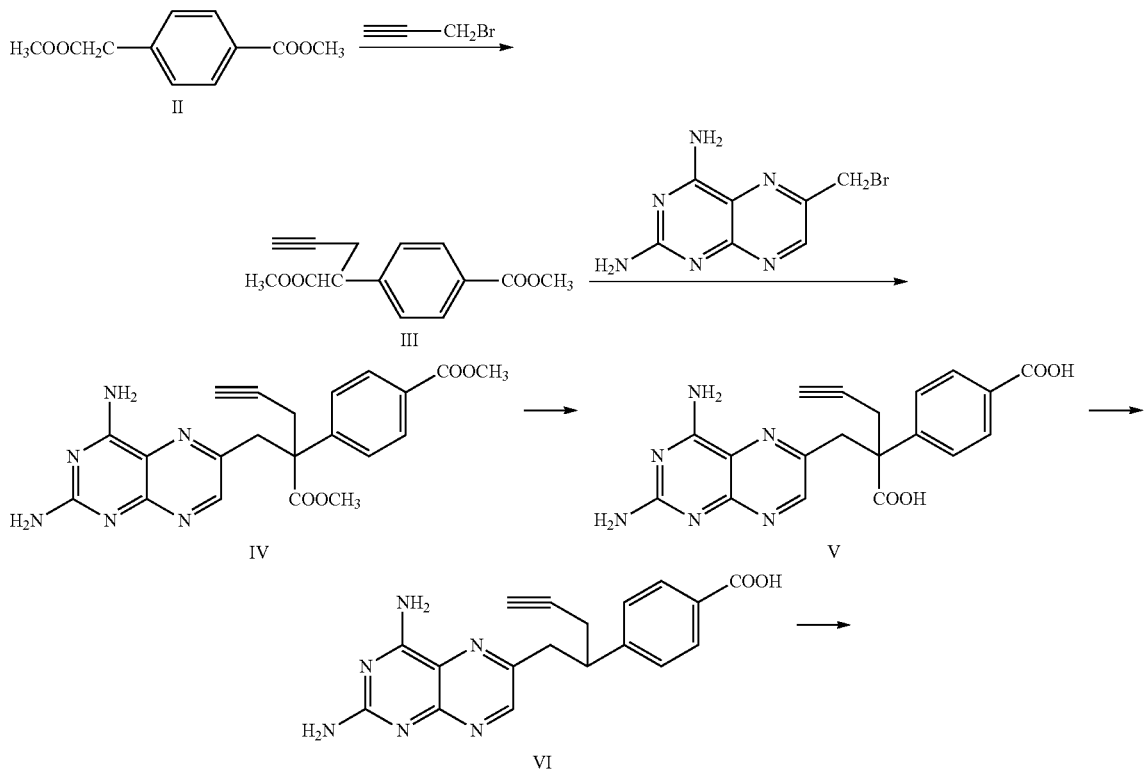

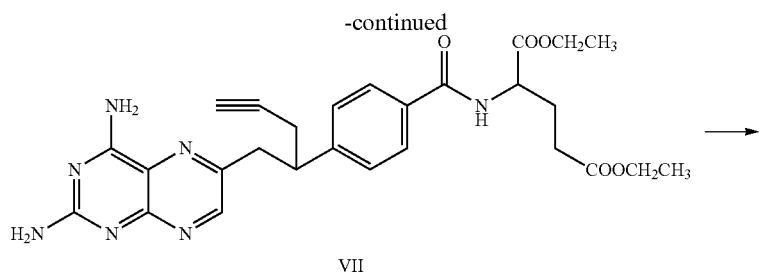

VII

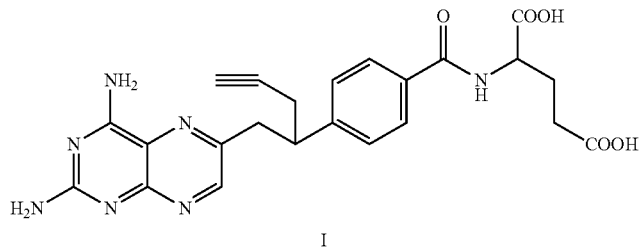

I

The methods disclosed in DeGraw et al., publication, U.S. Pat. No. 5,374,726 and U.S. Pat. No. 5,354,741 suffer from the following disadvantages, which are outlined below:
(i) Use of pyrophoric Potassium hydride in the initial alkylation step and the subsequent coupling step.
(ii) Amide formation in the penultimate step by use of a hazardous chloroformate reagent.
(iii) The final product has a purity of ~95% and is contaminated with the 10-deazaminopterin impurity to the level of 4%, which affects the final quality of Active Pharmaceutical ingredient (API) and does not meet the Pharmacopeial specifications.
(iv) Use of 2-methoxyethanol in the last step which is classified under guideline of International Conference on Harmonisation of Pharmaceutical for Human USE (ICH) as a Class-2 solvent, with a maximum daily exposure limit of 50 ppm.
(v) Extensive use of column chromatography during the method adding to the cost of manufacture.
(vi) Low yield of the final Pralatrexate (~5.5%).

U.S. Pat. No. 6,028,071 discloses a process for the preparation of Pralatrexate of Formula (I) comprising coupling of homoterephthalic acid dimethyl ester with propargyl bromide using NaH in THF, further coupling of the product with 2,4-diamino-6-bromomethylpteridine using NaH in DMF, followed by hydrolysis with a base in 2-methoxyethanol-water mixture, and decarboxylation at elevated temperatures at 115-120° C. in DMSO, and finally coupling of the product with L-glutamic acid dimethyl ester using benzotriazole-1-yloxytris(dimethylamino) phosphonium hexafluorophosphate (BOP) and triethylamine in DMF, and finally hydrolysis with NaOH in methanol-water mixture to yield Pralatrexate. The process is outlined below as synthetic Scheme-2.

Scheme-2

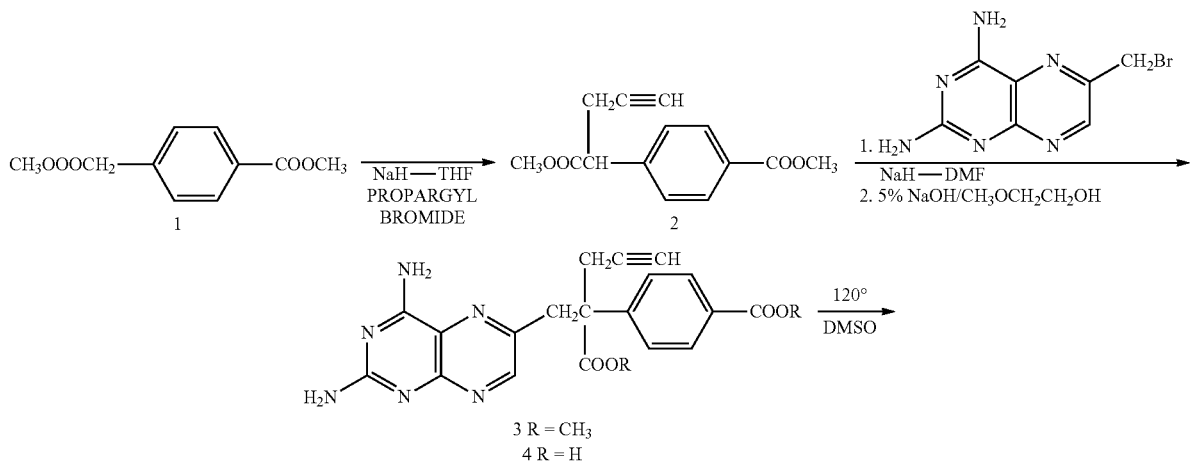

3 R = CH$_3$
4 R = H

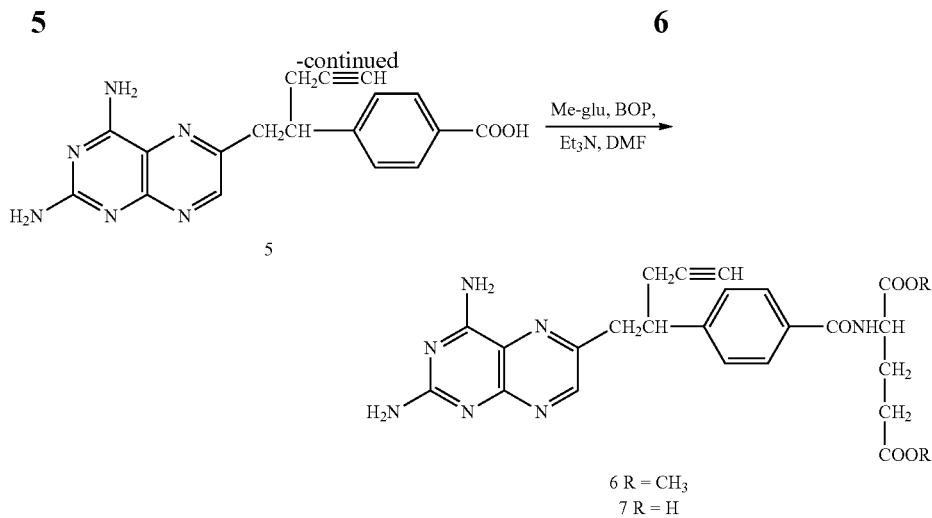

5

6 R = CH₃
7 R = H

The process disclosed in U.S. Pat. No. 6,028,071 suffer from the following disadvantages outlined below
(i) Use of sodium hydride in the initial alkylation step and the subsequent coupling step.
(ii) Using benzotriazole-1-yloxytris(dimethylamino) phosphonium hexafluoro phosphate (BOP) in coupling reaction that liberates Hexamethylphosphoramide (HMPA), which is carcinogenic
(iii) Extensive column chromatography during the process adding to the cost of manufacture
(iv) Quality of the API obtained by this process is only ~98%.
(v) Low yield of Pralatrexate is obtained (2.06%).
(vi) In the propargylation step the ratio of α-monopropargyl homoterephthalic acid dimethyl ester to α-monopropargyl homoterephthalic acid dimethyl ester is not less than 75:25.

US 20110190305 relates to optically pure diastereomers of 10-propargyl-10-deazaminopterin, in particular the two (R,S) diastereomers about the C10 position. None of the prior art discloses a process for preparing substantially pure Pralatrexate. When the present inventors practiced the invention disclosed in U.S. Pat. No. 6,028,071 to ascertain the purity of Pralatrexate, they found the content of individual diastereomers at the C10 position to be 50±3.66%.

Typically, drug substances that are racemic, preferably contain at least one chiral centre resulting in two diastereomers of equal proportion. Any substantial change in diastereomeric ratio may lead to loss of racemisation and may result in a drug substance with undesirable therapeutic effect. Consequently, there was a need to obtain a substantially pure racemic Pralatrexate, in particular the two diastereomers about the C10 position, wherein the content of each diastereomer is 50±0.6%. The process described within the instant invention resolves this issue.

Accordingly, there is a need in the art for improved methods for preparation of Pralatrexate which is a simple, convenient, economical, industrially viable commercial process and restricts the use of hazardous and expensive reagents and solvents and moreover, utilizes a simple and less laborious purification method, restricting the use of expensive column chromatography and results in the formation of Pralatrexate, in particular Pralatrexate obtained in high yields and of Pharmacopoeial grade having a purity.

In their endeavor to provide an improved process for manufacture of Pralatrexate of Formula (I), the present inventors found that most, if not all of the limitations of the prior art could be addressed through utilization of:
a) Novel intermediates for synthesis of the object compounds;
b) Less expensive, less hazardous reagents and solvents; and
c) Novel and simple purification methods, restricting the use of column chromatography.
d) Highly pure Pralatrexate of purity not less than 99% and overall high yield of not less than 11%.
e) Cost effective and robust process.

SUMMARY OF THE INVENTION

First aspect of the present invention provides a process for preparation of intermediate of Formula (III), useful for the preparation of Pralatrexate of Formula (I)

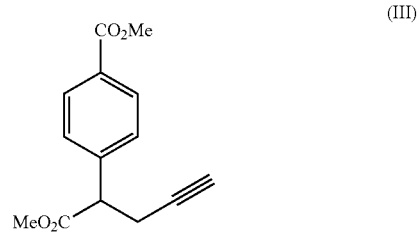 [SMILES: C#CCC(C(=O)OC)c1ccc(C(=O)OC)cc1]

(III)

comprising alkylating compound of Formula (II)

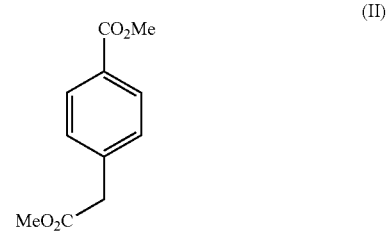 [SMILES: COC(=O)Cc1ccc(C(=O)OC)cc1]

(II)

with an alkylating agent in the presence of a suitable base.

Optionally purifying compound of Formula (III) with a suitable solvent.

Second aspect of the present invention provides a novel intermediate of Formula (V), wherein X is an acid.

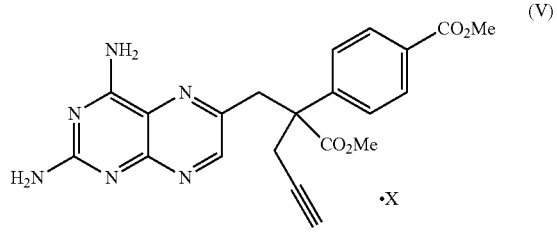 [SMILES: C#CCC(Cc1cnc2nc(N)nc(N)c2n1)(C(=O)OC)c1ccc(C(=O)OC)cc1 ; "·X"]

Third aspect of the present invention provides an acid addition salt of Formula (V')

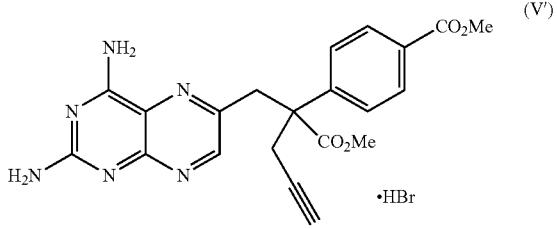 [SMILES: C#CCC(Cc1cnc2nc(N)nc(N)c2n1)(C(=O)OC)c1ccc(C(=O)OC)cc1 ; Br]

Fourth aspect of the present invention provides a process for preparation of intermediate of Formula (V), comprising the steps of;

a) coupling compound of Formula (III) with a compound of Formula (IV) or its acid addition salt

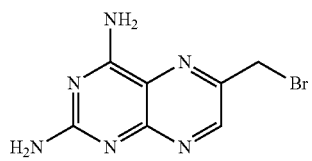

in presence of a base and suitable solvent.

b) treating the obtained compound with an acid to form intermediate of Formula (V)

c) Optionally converting it to compound of Formula VI

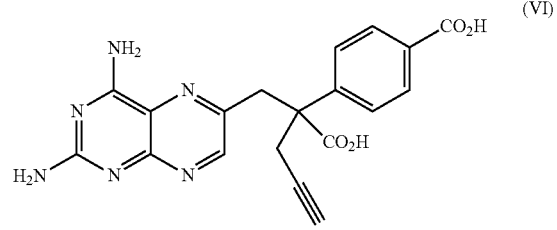 [SMILES: C#CCC(Cc1cnc2nc(N)nc(N)c2n1)(C(=O)O)c1ccc(C(=O)O)cc1]

Fifth aspect of the present invention provides a novel intermediate of Formula (VII), wherein Y is a base and n is 1 or 2.

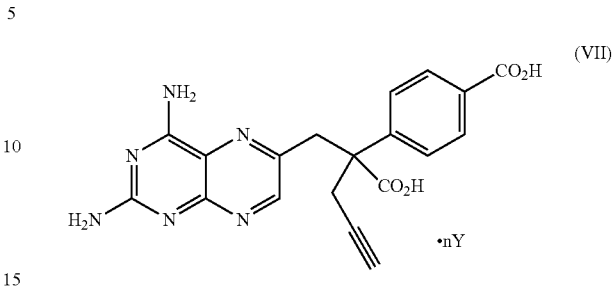

Sixth aspect of the present invention provides Dicyclohexyl amine salt of Formula (VII')

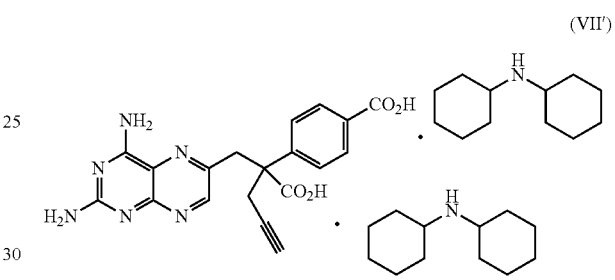

Seventh aspect of the present invention provides a process for preparation of the intermediate of Formula (VII)

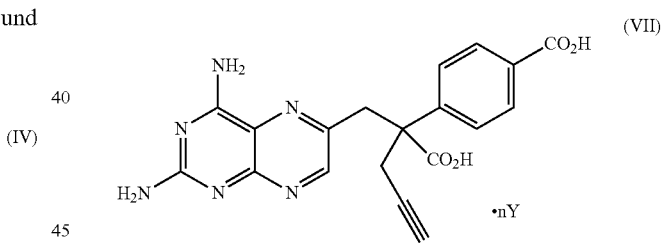

Wherein Y and n are as defined hereinabove, comprising the steps of:

a) treating compound of Formula (V) with a suitable base to obtain a compound of Formula (VI).

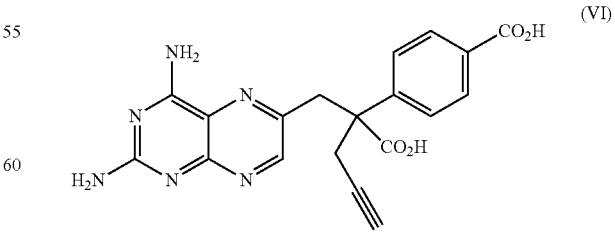

b) converting the compound of Formula (VI) to compound of Formula (VII) in the presence of a suitable base.

c) Optionally purifying the compound of Formula (VII) in a solvent or mixture of solvents.

Eighth aspect of the present invention provides a novel intermediate of Formula (VIII), wherein M is an alkali metal selected from the group comprising of sodium, lithium and potassium.

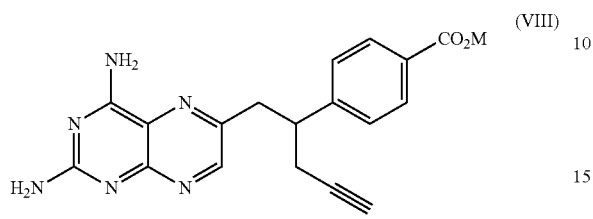

Ninth aspect of the present invention provides Sodium Salt of Formula (VIII')

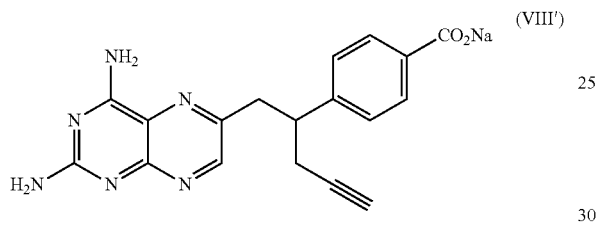

Tenth aspect of the present invention provides a process for preparation of the novel intermediate (VIII) comprising the steps of:
  a) decarboxylation of compound of Formula (VI) or compound of Formula (VII) in a suitable solvent.
  b) treating the obtained compound with a suitable base to obtain a compound of Formula (VIII)

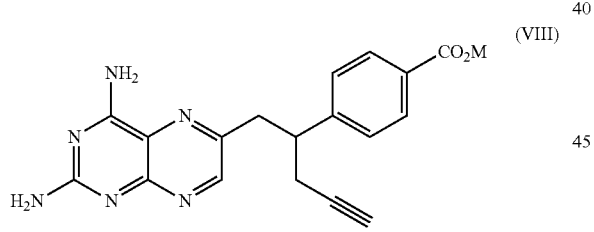

c) Optionally purifying the compound of Formula (VIII) with a suitable solvent or mixture of solvents.

Eleventh aspect of the present invention provides a process for the preparation of Pralatrexate of Formula (I)

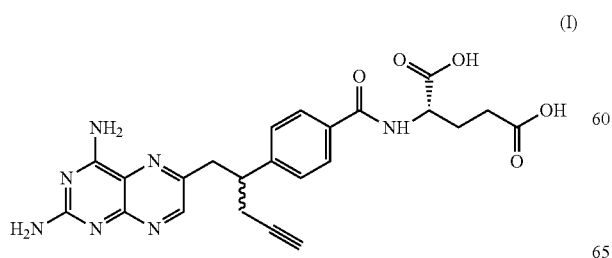

Comprising the steps of:
a) alkylating compound of Formula (II)

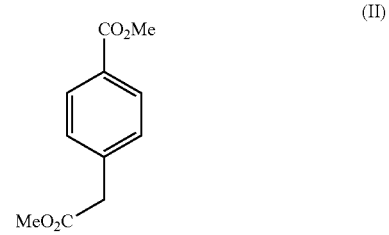 [SMILES: COC(=O)Cc1ccc(C(=O)OC)cc1]

with an alkylating agent in the presence of a suitable base to obtain a compound of Formula (III) and optionally purifying compound of Formula (III) with a suitable solvent.

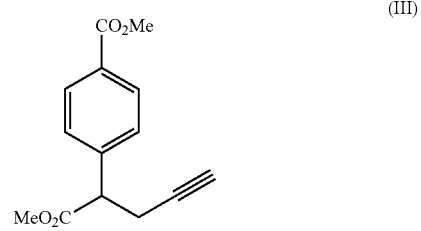 [SMILES: C#CCC(C(=O)OC)c1ccc(C(=O)OC)cc1]

b) Coupling compound of Formula (III) obtained in step (a) with a compound of Formula (IV) or its acid addition salt in presence of a base and a suitable solvent

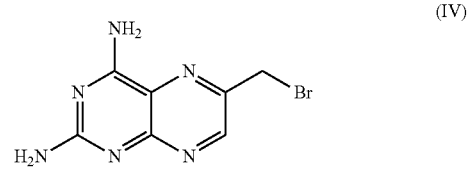 [SMILES: Nc1nc(N)c2nc(CBr)cnc2n1]

treating the obtained compound with an acid to form intermediate of Formula (V), wherein X is acid and optionally purifying compound of Formula (V) with a suitable solvent.

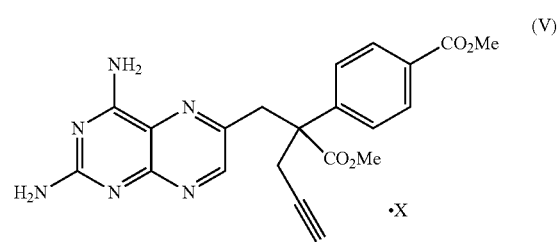 [SMILES: C#CCC(Cc1cnc2nc(N)nc(N)c2n1)(C(=O)OC)c1ccc(C(=O)OC)cc1 ; "·X"]

c) Converting intermediate of Formula (V) to compound of Formula VI in a suitable base

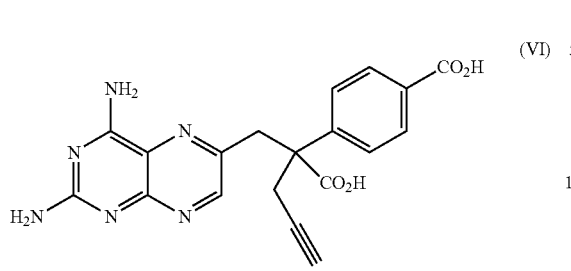

(VI)

d) Optionally converting the compound of Formula (VI) to compound of Formula (VII), Wherein Y is base and n is 1 or 2, in the presence of a suitable base and optionally purifying the compound of Formula (VII) in a solvent or mixture of solvents.

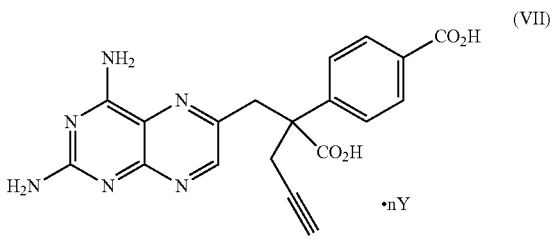

(VII)

e) decarboxylation of compound of Formula (VI) or compound of Formula (VII) in a suitable solvent and treating the obtained compound with a suitable base to obtain a compound of Formula (VIII), wherein M is an alkali metal as defined herein.

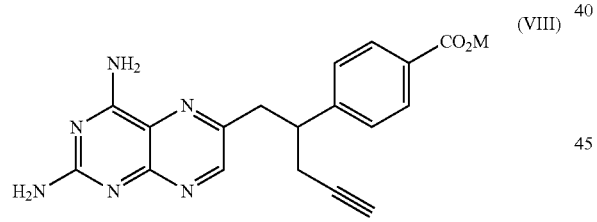

(VIII)

f) Optionally purifying the compound of Formula (VIII) with a suitable solvent or mixture of solvents.

g) Coupling compound of Formula (VIII) obtained in step (f) with a compound of Formula (IX)

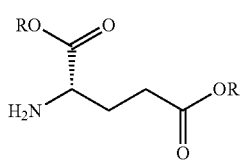

(IX)

in the presence of a suitable dehydrating agent and activating agent, wherein R is a C1-C4 alkyl group to obtain a compound of Formula (X)

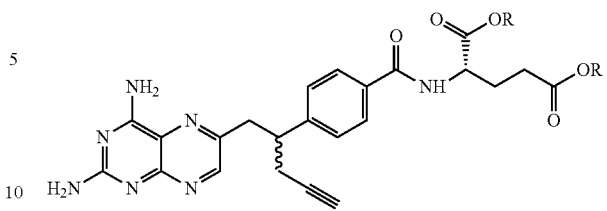

(X)

wherein R is as defined herein above.

h) Hydrolysing the compound of Formula (X) obtained in step (g) to obtain compound of Formula (I) in presence of a suitable base

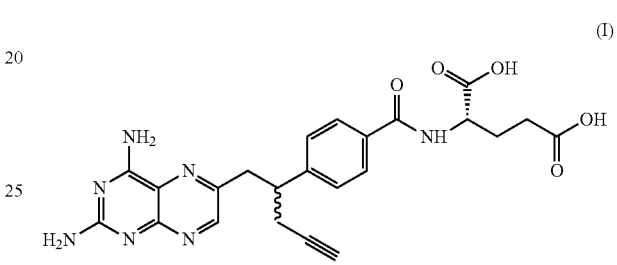

(I)

Twelfth aspect of the present invention provides a process for obtaining substantially pure Pralatrexate comprising the steps of
 a) Contacting Pralatrexate with a mixture of alcohol and halogenated hydrocarbon to obtain a mixture,
 b) Stirring the said mixture at ambient temperature,
 c) Collecting the solid,
 d) Contacting the said solid of step (c) with demineralized water to obtain a mixture.
 e) Stirring the said mixture of step (d) at ambient temperature.
 f) isolating the pure Pralatrexate.

Thirteenth aspect of the present invention provides a substantially pure Pralatrexate.

BRIEF DESCRIPTION OF THE DRAWINGS

FIG. 1 depicts the X-ray Powder diffractogram of Pralatrexate.

DETAILED DESCRIPTION OF THE INVENTION

The alkylation of Compound of Formula (II) may be carried out with an alkylating agent. Suitable alkylating agent may be selected from propargyl bromide, propargyl chloride and propargyl iodide. It is preferable to use a alkylating agent such as Propargyl bromide in the present process.

The alkylation of compound of Formula (II) may be carried out in the presence of a suitable base selected from the group comprising of metal carbonate such as lithium carbonate, sodium carbonate, potassium carbonate, barium carbonate, calcium carbonate and magnesium carbonate; metal bicarbonate such as sodium bicarbonate, potassium bicarbonate, barium bicarbonate, calcium bicarbonate and magnesium bicarbonate and metal hydroxide such as sodium hydroxide, potassium hydroxide, barium hydroxide, calcium hydroxide and magnesium hydroxide. The base may also be selected from the group comprising of C1-C4 alkyl ammonia; mono, di or tri C1-C4 alkyl amine such as triethyl amine, diisipropropyl ethyl amine; mono, di or tri hydroxy C1-C4 alkyl amine; morpholine; thiomorpholine; piperidine; N,N-dimethylaniline; pyridine; hydrazines and pyrrolidine.

It is preferable to use a base such as potassium carbonate in the present step of this process.

The alkylation of compound of Formula (II) may also be carried out in the presence of a Phase transfer Catalyst such as Quaternary Ammonium salt or Quaternary Phosphonium salt. Preferable Tetra Butyl ammonium iodide may be used in a particular Embodiment.

The alkylation of compound of Formula (II) may be carried out in the presence of a suitable solvent. Suitable solvent may be selected from the group comprising of water; alcohols, such as methanol, ethanol and isopropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone or mixtures thereof. It is preferable to use dimethylacetamide as the solvent in the present step of this process.

The alkylation of compound of Formula (II) may be carried out at about ambient temperature to about reflux temperature. The ambient temperature may be at about room temperature, which may range from about 20° to about 35° C.

The alkylation of compound of Formula (II) may be carried out for about 20 hour to about 40 hours. The compound of Formula (III) may be further purified with suitable solvent as defined herein.

Compound of Formula (V) may also be characterized using various techniques, as defined herein. Examples of acid in compound of Formula (V) are as defined herein.

The coupling of compound of Formula (III) with a compound of Formula (IV) may be carried out in presence of a suitable base selected from all group (I) and group (II) metal hydrides, alkyl lithium, and aryl lithium bases, as well as all group (I) and group (II) bases can be used for coupling. Examples include methyllithium, butyllithium, t-butyllithium, phenyllithium, sodium hydride, potassium hydride, and the like, to mention only a few. It is preferable to use a hydride base such as sodium hydride in the present process.

The compound of Formula (IV) may be purified with suitable solvent, prior to coupling reaction.

The coupling of compound of Formula (III) with a compound of Formula (IV) may be carried out in the presence of a suitable solvent. Suitable solvent may be selected from the group comprising of water; alcohols, such as methanol, ethanol and isopropanol; nitriles, such as acetonitrile; chlorinated hydrocarbons, such as dichloromethane, ethylenedichloride; dipolar aprotic solvents, such as dimethylsulfoxide, dimethylacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone or mixtures thereof. It is preferable to use a solvent such as Dimethylacetamide in the coupling.

The coupling of compound of Formula (III) may be carried out at a temperature of about −30 to 0° C. The temperature employed is preferably between −20 to −10° C.

The coupling of compound of Formula (III) may be carried out for about 2 hours to about 20 hours. Preferably between 2 to 6 hours.

The intermediate of Formula (V) may be obtained by reacting with an acid. Examples of acid include inorganic acids resulting in forming salts such as but not limited to hydrohalides (e.g.hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, pamoate, bitartrate, camphorsulfonate, edetate, 1,2ethanedisulfonate, fumarate, glucoheptonate, gluconate, glutamate, hexylresorcinate, hydroxynaphtoate, hydroxyethanesulfonate, mandelate, mefhylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutanedioic, 2-hydroxy-1,2,3-propanetricarboxylic and cyclohexanesulfamic acids and the like.

It is preferable to use a hydrohalide such as hydrobromide in the present process.

The formation of an addition salt of Formula (V) may be carried out in a suitable solvent. The suitable solvent may be selected from the group comprising of water; alcohols, such as methanol, ethanol and isopropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone or mixtures thereof.

Preferred solvent mixture is methanol, isopropanol and dichloromethane.

Formation of an addition salt of Formula (V) may be carried out at a temperature of about −30 to 30° C. Preferably the temperature is between 0-5° C.

The addition salt may be optionally purified using a suitable solvent selected from the group comprising of water; alcohols, such as methanol, ethanol and isopropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone or mixtures thereof.

Compound of Formula (V) may be characterized using various techniques, as defined herein.

Conversion of compound of Formula (V) to compound of Formula (VI) may be carried out in presence of a base. Suitable base may be selected from the group comprising of Ammonium hydroxide, sodium hydroxide, potassium hydroxide, Lithium hydroxide, Cesium hydroxide and Rubidium hydroxide. The preferred base is potassium hydroxide.

The conversion reaction may be carried out in the presence of a suitable solvent. Suitable solvent may be selected from the group comprising of water; alcohols, such as methanol, ethanol and isopropanol, 2-methoxyethanol, 2-ethoxyethanol, 2-methoxypropanol, 3-methoxypropanol, 3-ethoxypropanol, and 3-ethoxypropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone and mixtures thereof.

Preferred solvent in this step is mixture of water and 2-methoxyethanol. More Preferred solvent in this step is water.

Compound of Formula (VI) may be optionally purified in the presence of a suitable solvent. Suitable solvent may be selected from the group comprising of water; alcohols, such as methanol, ethanol and isopropanol, 2-methoxyethanol, 2-ethoxyethanol, 2-methoxypropanol, 3-methoxypropanol, 3-ethoxypropanol, and 3-ethoxypropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone and mixtures thereof.

Preferred solvent for purification in this step is isopropanol.

The compound of Formula (VI) may be converted to compound of Formula (VII) in the presence of suitable base. Examples of suitable base include inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylene-diamine, chloroprocaine, choline, diethanolamine, ethylene-diamine, N-methyl-glucamine, 1,5-diazabicyclo[5.4.0]undecene, piperidine, ethanolamine, pyrrolidine, morpholine, piperazine, cyclohexaneamine, procaine, dicyclohexylamine and the like.

The preferred base used in this step is dicyclohexylamine.

The formation of compound of Formula (VII) may be carried out in presence of a suitable solvent. Suitable solvent may be selected from the group comprising of water; alcohols, such as methanol, ethanol and isopropanol, 2-methoxyethanol, 2-ethoxyethanol, 2-methoxypropanol, 3-methoxypropanol, 3-ethoxypropanol, and 3-ethoxypropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone and mixtures thereof.

It is preferable to use a solvent such as Methanol in the present process.

Compound of Formula (VII) may be characterized using various techniques, as defined herein.

Decarboxylation of compound of Formula (VI) or compound of Formula (VII) may be carried out in a suitable solvent and in presence or absence of base.

Suitable solvents may include both aprotic, polar organic solvents and protic, polar organic solvents. A single protic, polar solvent or a single aprotic, polar solvent may be used. Additionally, mixtures of aprotic, polar solvents, mixtures of protic, polar solvents, mixtures of aprotic and protic, polar solvents, and mixtures of aprotic or protic solvents with nonpolar solvents may be used, wherein aprotic, polar solvents or mixtures thereof are preferred. Suitable aprotic, polar solvents include, but are not limited to, dimethylformamide, 1-methyl-2-pyrrolidinone, dimethylacetamide, dimethylsulfoxide, hexamethylphosphoramide, and hexamethylphosphorous triamide. Suitable protic, polar solvents include, but are not limited to, di(propylene glycol)methyl ether (Dowanol TM DPM), di(ethylene glycol)mefhyl ether, 2-butoxyethanol, ethylene glycol, 2-mefhoxyethanol, propylene glycol methyl ether, n-hexanol, and n-butanol.

In this process N,N-dimethylacetamide or dimethylsulfoxide are preferred solvents for decarboxyaltion.

The product obtained by Decarboxylation may be further treated with suitable base to obtain compound of Formula (VIII), wherein M is alkali metal. Examples of base include inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylene-diamine, chloroprocaine, choline, diethanolamine, ethylenediamine, N-methyl-glucamine, 1,5-diaz abicyclo[5.4.0] undecene, piperidine, ethanolamine, pyrrolidine, morpholine, piperazine, cyclohexaneamine, procaine, dicyclohexylamine and the like.

In this step the preferred base is Sodium Hydroxide.

Compound of Formula (VIII) may be optionally purified with suitable solvent. Suitable solvent may be selected from the group comprising of water; alcohols, such as methanol, ethanol and isopropanol, 2-methoxyethanol, 2-ethoxyethanol, 2-methoxypropanol, 3-methoxypropanol, 3-ethoxypropanol, and 3-ethoxypropanol; nitriles, such as acetonitrile; chlorinated hydrocarbons, such as dichloromethane, ethylenedichloride; dipolar aprotic solvents, such as dimethylsulfoxide, dimethyacetamide and dimethylformamide; esters, such as ethyl acetate and isopropyl acetate; cyclic ethers, such as dioxane and tetrahydrofuran; ketone such as acetone, diisobutyl ketone, cyclohexanone, methylcyclohexanone, methyl ethyl ketone, methyl isobutyl ketone, acetylacetone and mixtures thereof.

Preferred solvent for purification in this step is mixture of isopropanol and water.

Compound of Formula (VIII) may be characterized using various techniques, as defined herein.

Coupling reaction of the compound of Formula (VIII) with a compound of Formula (IX) may be carried out in presence of dehydrating and activating agent. Dehydrating agent may be selected from dicyclohexylcarbodiimide (DCC) for example, or more preferably 1-(3-dimethylaminopropyl)-3-ethylcarbodiimide hydrochloride (EDAC). In addition, the presence of a suitable activating agent, such as 1-hydroxybenztriazole (HOBt) is usually required to promote efficient coupling of the carboxylic acid to the appropriate amine. It is preferable to use HOBt as the activating agent.

The reaction may be additionally carried out in presence of a base such as triethylamine, butyl amine, pyridine, isobutylamine, diisobutyl amine, isopropyl amine, diisopropyl amine, diisopropyl ethyl amine. Preferably the base is diisopropyl ethyl amine.

Coupling reaction of the compound of Formula (VIII) may be typically carried out in an aprotic solvent such as acetonitrile, tetrahydrofuran, dimethylsulfoxide, hexamethylphosphoramide, hexamethylphosphorous triamide, 1-methyl-2-pyrrolidinone, N,N-dimethylformamide (DMF), or more preferably N,N-dimethylacetamide to obtain a compound of Formula (X), wherein R is a C1-C4 alkyl group, preferably R is methyl group.

The coupling reaction of compound of Formula (VIII) may be carried out in a temperature range of 0-60° C. Preferably the reaction is carried out in between 0-25° C. More preferably the temperature is between 0-10° C.

Hydrolysis reaction of compound of Formula (X) may be carried out in presence of a suitable base. Suitable bases include, but are not limited to, potassium hydroxide, barium hydroxide, cesium hydroxide, sodium hydroxide, strontium hydroxide, calcium hydroxide, lithium hydroxide, and rubidium hydroxide, cyclohexamine, 1,5-diazabicyclo[5.4.0]undecene, piperidine, ethanolamine, pyrrolidine, diethylamine, morpholine, piperazine, dicyclohexylamine, hydroxylamine, N,N'-isopropylamine, tributlyamine, triethylenediamine, monoethanolamine, diethanolamine, and triethanolamine. The preferred base is Sodium Hydroxide.

The process for obtaining substantially pure Pralatrexate may be carried out by contacting with a mixture of alcohol and halogenated hydrocarbon. Halogenated hydrocarbons may be selected from, such as dichloromethane, ethylenedichloride, chloroform. Alcohols, may be selected from, such as methanol, ethanol and isopropanol.

In a preferred embodiment, said mixture of methanol and dichloromethane has about a 1:3 volume ratio.

In a more preferred embodiment, said mixture of methanol and dichloromethane has about a 1:9 volume ratio.

The stirring may be carried out at ambient temperature. The ambient temperature employed is preferably between 15 to 30° C.

The stirring may be carried out for about 1 hour to about 20 hours. Preferably it is between 2 to 4 hours.

In a preferred embodiment, said mixture formed in step (b) is stirred at ambient temperature of about 15-30° C.

In a preferred embodiment, said mixture formed in step (b) is stirred at ambient temperature of about 15-30° C. for about 4 hours.

In a preferred embodiment, said mixture so formed in step (b) is collected by filtration.

In a preferred embodiment, said mixture so formed in step (b) is collected by evaporation of solvents or solvent mixtures thereof.

The said solid obtained in step (c) is contacted with demineralized water to obtain a mixture.

The contacting may be carried out for about 1 hour to about 20 hours. Preferably it is between 2 to 4 hours.

In a preferred embodiment, said mixture formed in step (d) is stirred at ambient temperature. The ambient temperature employed is preferably between 15 to 30° C.

In a preferred embodiment, said mixture formed in step (d) is stirred at ambient temperature for about 1 hour to about 20 hours. Preferably it is between 2 to 4 hours.

In a preferred embodiment, the pure pralatrexate may be isolated from the said mixture of step (d) by filtration.

In a preferred embodiment, the pure pralatrexate may be isolated from the said mixture of step (d) by evaporation of solvents or solvent mixtures thereof.

Optionally, washing the solid with a suitable solvent or mixture of solvents thereof.

Suitable solvent may be selected from the group comprising of water; alcohols, such as methanol, ethanol and isopropanol; Halogenated hydrocarbons, such as Dichloromethane, ethylenedichloride, chloroform; esters, such as ethyl acetate and isopropyl acetate; ketone such as acetone, diisobutyl ketone, cyclohexanone, methylcyclohexanone, methyl ethyl ketone, methyl isobutyl ketone, acetylacetone or mixtures thereof.

The term "contacting" is used herein to refer to the act of mixing, slurrying, dissolving, or otherwise contacted in some other manner.

The term "ambient temperature," as used here means about 15-30° C.

The term "substantially pure Pralatrexate" as used herein, means the racemic mixture, wherein the content of each diastereomer at C10 position, is 50±0.6%.

The term "substantially pure Pralatrexate" as used herein, also includes the racemic mixture particularly the two diastereomers at C10 position, having a high performance liquid chromatography (HPLC) purity of not less than 99.5% and having less than 0.1% of impurities.

Unacceptable amounts of impurities are generally formed during the preparation of Pralatrexate and have been characterized to have the structures (Impurity 1 to Impurity 4).

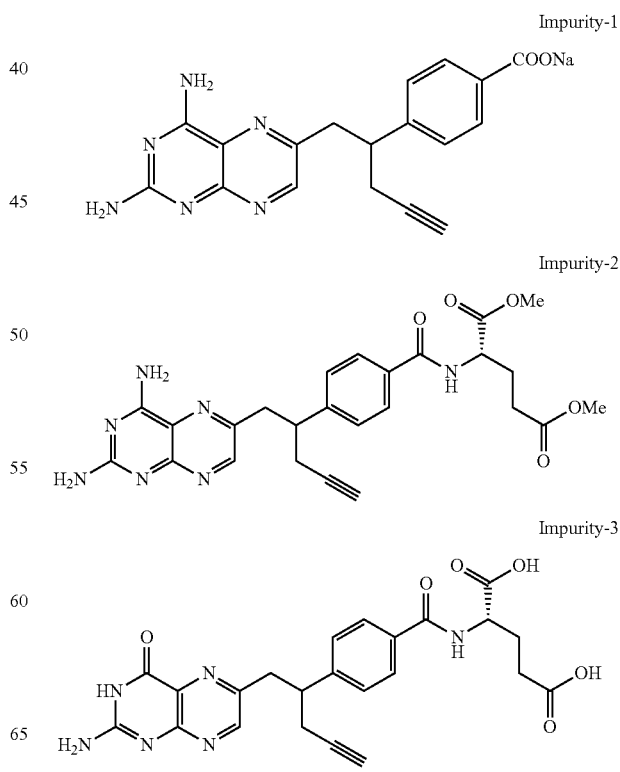

Impurity-4

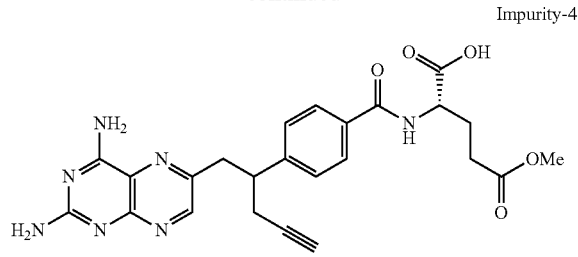

In order to determine the relative amounts of the diastereomers in the product it is analyzed using standard chiral and achiral liquid chromatography techniques. Chiral high performance liquid chromatography (HPLC) may be used to determine the relative proportions of each diastereomer.

Pralatrexate of Formula (I) may be characterized using various techniques, which are well known to those of ordinary skill in the art. Examples of characterization methods include, but are not limited to, single crystal X-ray diffraction, powder X-ray diffraction (PXRD), simulated powder X-ray patterns, differential scanning calorimetry (DSC), solid-state $^{13}$C-NMR, $^{1}$H-NMR, Raman spectroscopy, infrared spectroscopy, moisture sorption isotherms, thermal gravimetric analysis (TGA), chiral and achiral HPLC techniques and hot stage techniques.

The Detailed experimental parameters suitable for this process of making Pralatrexate are provided by the following examples, which are intended to be illustrative and not limiting of all possible aspects of the invention.

Example-1

α-Propargylhomoterephthalic Acid Dimethyl Ester

To a mixture of K$_2$CO$_3$ (398.6 g), homoterephthalic acid dimethyl ester (200 g) in DMAc (1000 mL), propargyl bromide (257.24 g) was added followed by TBAI (17.72 g) at 25-30° C. and stirred for 20-26 hours. The reaction was monitored by HPLC and found the ratio of Monopropargyl homoterephthalic Acid Dimethyl Ester to that of dipropargyl homoterephthalic Acid Dimethyl Ester to be not less than 85:15. After 26 hours the reaction mixture was quenched with DM water (2000 ml) and extracted with ethyl acetate (2×2000 ml). The organic layer was separated and back-extracted with DM water (1000 ml). The organic layer was then evaporated to dryness at reduced pressure on a rotary evaporator (below 60° C.). Further IPA (1000 ml) was added to the residue and evaporated to dryness at 45-50° C. under vacuum. The crude product was purified by dissolving in IPA twice (1000 ml, 600 ml) at 45-50° C., followed by cooling to 0-5° C. and stirred for 1-3 hours. The product was filtered and dried under vacuum at 40-45° C. to give 166 g (70.2%) of the title compound.
Assay: 91.72%
Monopropargyl homoterephthalic Acid Dimethyl Ester: 87.8%
Dipropargyl homoterephthalic Acid Dimethyl Ester: 6.4%

Example-2

α-Propargylhomoterephthalic Acid Dimethyl Ester

To a mixture of K$_2$CO$_3$ (1194.5 g), homoterephthalic acid dimethyl ester (600 g) in DMAc (3000 mL), propargyl bromide (582.43 g) was added followed by TBAI (106.41 g) at 25-30° C. and stirred for 20-26 hours. The reaction was monitored by HPLC and found the ratio of Monopropargyl homoterephthalic Acid Dimethyl Ester to that of dipropargyl homoterephthalic Acid Dimethyl Ester to be not less than 85:15. After 26 hours the reaction mixture was quenched with DM water (3000 ml) and extracted with ethyl acetate (2×3000 ml). The organic layer was separated and back-extracted with DM water (3000 ml). The organic layer was then evaporated to dryness at reduced pressure on a rotary evaporator (below 60° C.). Further IPA (1000 ml) was added to the residue and evaporated to dryness at reduced pressure. The crude product was crystallized by dissolving in IPA (000 ml) at 45-50° C. and cooled to 0-5° C. and stirred for 1-2 hours. The product was vacuum filtered. The product obtained was further crystallized with IPA (1800 ml) saturated with Ethyl acetate (54 ml) by dissolving at 55-60° C. and stirred at 20-25° C. for 2-3 hours, followed by stirring at 0-5° C. for 2-3 hours. The solid was filtered and dried under vacuum at 40-45° C. to give 466 g (65.6%) of the title compound.
Purity: 99.19%

Example-3

10-Propargyl-10-carbomethoxy-4-deoxy-4-amino-10-deazapteroic Acid Methyl Ester hydrobromide salt Propargylhomoterephthalic Acid Dimethyl Ester (50 g) was added to 2,4-diamino-6-bromomethylpteridine hydrobromide (98.87 g) in DMAc (600 mL) at −20 to −15° C. To this NaH (17.84 g) was added in four lots at −20 to −10° C. and stirred for 3-4 hours. The reaction was monitored by HPLC and quenched by slow addition of a mixture of acetic acid (46.88 mL) in ethyl acetate (250 mL) at −15 to 0° C. To this DM water (3500 mL) was added and stirred for 14-15 h at 20-25° C. The solid obtained was filtered and dried under vacuum at 60-65° C. For the HBr salt preparation, a solvent mixture of MeOH (110 mL), IPA (165 mL) and DCM (330 mL) was prepared and to 517.5 ml of this solvent mixture 10-Propargyl-10-carbomethoxy-4-deoxy-4-amino-10-deazapteroic Acid Methyl Ester was added, followed by slow addition of 47% Aqueous HBr (122.41 g) at 20-30° C. The reaction mass was cooled to 0-5° C. and stirred for 1-2 hours. The Solid was filtered and dried under vacuum at 60-65° C. to give 75 g (73.7%) of the title compound.
Purity: 97.06%

Example-4

10-Propargyl-10-carbomethoxy-4-deoxy-4-amino-10-deazapteroic Acid Methyl Ester hydrobromide salt Propargylhomoterephthalic Acid Dimethyl Ester (200 g) was added to 2,4-diamino-6-bromomethylpteridine hydrobromide (337.5 g) in DMAc (2000 mL) at −20 to −15° C. To this NaH (84.45 g) was added in four lots at −20 to −10° C. and stirred for 3-4 hours. The reaction was monitored by HPLC and quenched by slow addition of a mixture of acetic acid (192.92 g) in DMAc (200 mL) at −15 to 0° C. To this DM water (4400 mL) was added and stirred for 14-15 h at 20-25° C. The solid obtained was filtered and dried under vacuum at 60-65° C.

For the HBr salt preparation, a solvent mixture of MeOH (440 mL), IPA (660 mL) and DCM (1320 mL) was prepared and to 2070 ml of this solvent mixture 10-Propargyl-10- carbomethoxy-4-deoxy-4-amino-10-deazapteroic Acid Methyl Ester was added, followed by slow addition of 47% Aqueous HBr (279.62 g) at 0-5° C. The reaction mass was stirred at 0-5° C. for 5-6 hours. The Solid was filtered and added to DCM (2000 mL) at 20-25° C. and stirred for 1-2 hours. The solid was filtered and dried under vacuum at 60-65° C. to give 285 g (70%) of the title compound.

Purity: 95.71%

$^1$H NMR (DMSO-d6; 400 MHz): δ 2.92 (t, J=2.4 Hz, 1H), 2.97 (dd, J=16.8 Hz & 2.4 Hz, 1H), 3.13 (dd, J=16.8 Hz & 2.4 Hz, 1H), 3.62 (s, 3H), 3.74 & 3.82 (2×d, J=14.8 Hz each, 2H), 3.84 (s, 3H), 7.44 (d, J=8.0 Hz, 2H), 7.46 (bs, 1H, NH), 7.92 (d, J=8.0 Hz, 2H), 8.15 (s, 1H, NH), 8.52 (s, 1H), 8.69 (bs, 1H, NH), 9.35 (s, 1H, NH), 12.86 (bs, 1H, HBr).

MS (ES+) m/z: 421 [M]$^+$.

Example-5

10-Propargyl-10-carboxy-4-deoxy-4-amino-10-deazapteroic Acid

To a solution of KOH (118.5 g) in DM water (400 mL) and 2-methoxyethanol (800 mL), 10-Propargyl-10-carbomethoxy-4-deoxy-4-amino-10-deazapteroic Acid Methyl Ester hydrobromide salt (50.0 g) was added and stirred the reaction mixture at 25-30° C. for 6 hours. Upon completion the reaction mixture was cooled to 5-10° C. and extracted with Ethylacetate two times (1375 mL, 625 mL). To the aqueous fraction, aqueous Acetic acid solution (149.6 mL acetic acid in 625 mL DM water) was added slowly at 5-10° C., followed by dilution with DM water (375 mL). The aqueous fraction was stirred for 15-16 h at 20-25° C., followed by stirring at 0-5° C. for 1-2 hours. The solid was filtered and dried under vacuum at 65-70° C. to give 34.3 g (87.6%) of the title compound.

Purity: 97.16%

Example-6

10-Propargyl-10-carboxy-4-deoxy-4-amino-10-deazapteroic Acid

To 10-Propargyl-10-carbomethoxy-4-deoxy-4-amino-10-deazapteroic Acid Methyl Ester hydrobromide salt (200 g) in DM water (1000 mL), was added a solution of KOH (184.30 g) in DM water (1000 mL) and stirred the reaction mixture at 20-25° C. for 4 hours. Upon completion glacial acetic acid (105 g) was added to the reaction mixture, followed by DM water (400 mL) and IPA (1800 mL). To this a further amount of glacial acetic acid (134.56 g) was added and stirred at 20-25° C. for 15 hours. The solid was filtered and dried under vacuum at 40-45° C. C to give 140 g (89.4%) of the title compound.

Purity: 96.33%

Example-7

10-Propargyl-10-carboxy-4-deoxy-4-amino-10-deazapteroic Acid dicyclohexylamine salt To 10-Propargyl-10-carboxy-4-deoxy-4-amino-10-deazapteroic Acid (200 g) in MeOH (1200 mL) cooled at 0-5° C. was added a solution of dicyclohexylamine (184.85 g) in MeOH (200 mL) and stirred for 3-4 hours at 0-5° C., and filtered the solid. The solid obtained was purified by stirring with acetone (2000 mL) at 20-25° C. for 1 hour and filtered. The solid was further purified by dissolving in a mixture of MeOH (5580 mL) and DCM (620 mL) at 35-40° C. The solution was distilled under vacuum till about 1300-1400 mL was remaining and cooled the resulting slurry to 0-5° C. and stirred for 1 hour, followed by filtration of solid and drying the solid under vacuum at 40-45° C. to give 282 g (73.3%) of the title compound.

Purity: 99.6%

$^1$H NMR (DMSO-d6; 400 MHz): δ 1.04 (m, 4H), 1.16 (m, 16H), 1.53-1.56 (m, 4H), 1.61-1.67 (m, 8H), 1.84-1.87 (m, 8H), 2.61 (bs, 1H), 2.74-2.80 (m, 6H), 3.48 (d, J=14.0 Hz, 1H), 3.67 (d, J=14.0 Hz, 1H), 6.56 (bs, 2H, NH$_2$), 6.70 (bs, 1H, NH), 7.42 (d, J=8.4 Hz, 2H), 7.68 (bs, 1H, NH), 7.78 (d, J=8.4 Hz, 2H), 8.48 (s, 1H).

MS (ES+) m/z: 182 [M+11]$^+$.

IR (KBr, cm$^{-1}$): 1540, 1557, 1639, 1704, 3300, 3420.

Example-8

10-Propargyl-4-deoxy-4-amino-10-deazapteroic Acid sodium salt

A solution of 10-Propargyl-10-carboxy-4-amino-10-deazapteroic Acid (40 g) in DMSO (400 mL) was added to preheated DMSO (1400 mL) at 110-115° C. and stirred for 20-30 min. The reaction was monitored by HPLC and upon completion; the reaction mixture was concentrated to dryness under vacuum below 90° C. IPA (600 mL) was added to the residue and heated to 50-55° C. for 2-3 hours, subsequently cooled to 20-25° C. and vacuum filtered the solid.

For preparing sodium salt of the acid the solid obtained was added to DM water (100 mL), followed by dropwise addition of aqueous NaOH solution (6.11 g NaOH in 300 mL DM water) at 10-15° C. The reaction mass was further cooled to 0-5° C. and stirred for 2-3 hours. The solid was filtered under vacuum. The solid obtained was purified by dissolving in a mixture of DM water (320 mL) and IPA (640 mL) at 75-85° C. The clear solution was filtered through Celite bed (20 g). The filtrate was cooled slowly to 0-5° C. and stirred for 1-2 hours. The solid obtained was filtered and dried under vacuum at 60-65° C. to give 19 g (50.3%) of the title compound.

Purity: 99.3%

Example-9

10-Propargyl-4-deoxy-4-amino-10-deazapteroic Acid sodium salt

10-Propargyl-10-carboxy-4-deoxy-4-amino-10-deazapteroic Acid dicyclohexylamine salt (25 g) was added to preheated DMAc (625 mL) at 50-55° C. and stirred at 105-110° C. stirred for 1 hour. The reaction was monitored by HPLC and upon completion, the reaction mixture was concentrated to dryness under vacuum below 70° C. The reaction mixture was diluted with DM water (150 mL), followed by dropwise addition of aqueous NaOH solution (1.45 g NaOH in 100 mL DM water) at 10-15° C. The reaction mass was further cooled to 0-5° C. and stirred for 2-3 hours. The solid was filtered under vacuum. The solid obtained was purified by obtaining a solution in a mixture of DM water (125 mL) and IPA (250 mL) heated to 75-85° C. The filtrate was cooled slowly to 0-5° C. and stirred for 1-2 hours. The solid obtained was filtered and dried under vacuum at 60-65° C. to give 10 g (81.5%) of the title compound.

Purity: 96.33%

$^1$H NMR (DMSO-d6; 400 MHz): δ 2.52-2.54 (m, 2H), 2.76 (bs, 1H), 3.12 (dd, J=14.0 Hz & 8.8 Hz, 1H), 3.24 (dd, J=14.0 Hz & 6.0 Hz, 1H), 3.47 (quintet, J=7.2 Hz, 1H), 6.52 (bs, 2H, NH$_2$), 7.16 (d, J=8.0 Hz, 2H), 7.49 (bs, 1H, NH), 7.58 (bs, 1H, NH), 7.71 (d, J=8.0 Hz, 2H), 8.33 (s, 1H).

MS (ES+) m/z: 349 [M+11]$^+$.

IR (KBr, cm$^{-1}$): 1558, 1593, 1623, 3378.

Example-10

10-Propargyl-10-deazaminopterin Dimethyl Ester

To 10-Propargyl-4-deoxy-4-amino-10-deazapteroic Acid sodium salt (35 g) in DMAc (280 mL) at 0-5° C. under nitrogen, was added HOBT (14.0 g) followed by EDAC.HCl (28.9 g) at 0-5° C. and stirred for 30 minutes. L-glutamic acid dimethyl ester (48.0 g) was added to the reaction mixture followed by DIPEA (37.8 g) at 0-5° C. The reaction mass was stirred for 21 hours at 20-25° C. The completion of reaction was monitored by HPLC and added DM water (100 mL) slowly to the reaction mixture at 5-15° C. and stirred for 30 minutes. Aqueous NaHCO$_3$ Solution (27.7 g of sodium bicarbonate in 250 mL of DM water) was added to the reaction mass at 5-15° C. for 30-40 min. DM water (700 mL) was added at 5-15° C. and stirred for 2-3 hours. The solid obtained was filtered. The crude product was purified by column chromatography over silica gel using a mixture of Methanol and Dichloromethane saturated with few drops of Triethylamine. The pure fractions were collected and the eluent was evaporated yielding to give 32 g (67%) of the title compound.

Purity: 99.75%

Example-11

10-Propargyl-10-deazaminopterin (Pralatrexate)

To aqueous NaOH (11.6 g NaOH in 472 mL DM water) and Methanol (944 mL), 10-Propargyl-10-deazaminopterin Dimethyl Ester (59.0 g) was added at 20-25° C. and stirred the reaction mass for 8 hours. After completion of reaction which was monitored by HPLC, pH of the reaction mass was adjusted to 6.6 with acetic acid. Excess methanol was evaporated under reduced pressure below 40° C. and DM water (1298 mL) was added to the residual solution. The pH of the residual solution was adjusted to 4.5 with dilute acetic acid. The reaction mass was stirred for 30 minutes at 20-25° C. and filtered the solid precipitated. The solid was furthered purified with DM water (590 mL) by stirring at 20-25° C. for 30-35 minutes. The solid was filtered and dried under vacuum at 35-40° C. to give 39 g (70%) of the title compound.

Purity: 99.56%

Water content=4.8% (w/w)

$^1$H NMR (DMSO-d6; 400 MHz): δ 1.91 (m, 1H), 2.05 (m, 1H), 2.33 (t, J=7.2 Hz, 2H), 2.59 (bm, 2H), 2.78 (s, 1H), 3.14-3.20 (bm, 1H), 3.28 (dd, J=14.4 Hz & 6.4 Hz, 1H), 3.64 (quintet, J=7.2 Hz), 4.35 (bm, 1H), 6.30 (bs, 2H, NH$_2$), 7.39 (d, J=8.0 Hz, 2H), 7.61 & 7.63 (2×bs, 2H, NH$_2$), 7.73 (d, J=8.0 Hz, 2H), 8.39 (bs, 1H), 8.50 (d, J=7.6 Hz, 1H, NH), 12.20 (bs, 2H, 2×CO$_2$H).

$^{13}$C NMR (DMSO-d6; 100 MHz): δ 24.84 (CH$_2$), 25.94 (CH$_2$), 30.46 (CH$_2$), 39.08 (CH$_2$), 43.05 (CH), 51.93 (CH), 72.90 (CH), 82.57 (C), 121.51 (C), 127.35 (2×CH), 127.35 (2×CH), 132.22 (C), 146.69 (C), 147.20 (C), 150.56 (CH), 154.17 (C), 162.41 (C), 162.77 (C), 166.42 & 166.46 (CONH), 173.54 (CO$_2$H), 173.94 (CO$_2$H).

MS (ES+) m/z: 478 [M+H]$^+$.

IR (KBr, cm$^{-1}$): 1540, 1557, 1639, 1704, 3300, 3420.

XRD (°2Theta; Cu): 8.47, 10.85, 12.28, 14.34, 15.00, 15.78, 18.90, 21.79, 24.20, 27.5, 28.92, 34.28.

Example-12 discloses the preparation of Pralatrexate according to U.S. Pat. No. 6,028,071.

Example-12

To 10-Propargyl-10-deazaminopterin dimethyl ester (3.0 g) in methanol (181.8 mL), aqueous sodium hydroxide (0.52 g of sodium hydroxide in 13.1 mL demineralized water) was added at 20-25° C. accompanied by stirring. The reaction mixture was stirred for 2 h at 20-25° C., kept for further 8 hours at the same temperature and diluted with demineralized water (181.8 mL). methanol was recovered under vacuum below 40° C. and the residue was left at 20-25° C. for 24 hrs. The reaction was monitored by HPLC and acidified with acetic acid (7.5 mL). The solid obtained was filtered, washed with demineralized water (15 mL) and suck-dried for 2-3 hrs. The product was dried under vacuum at 50-55° C. for 12 hours.

Weight: 2.5

Yield (%): 89.2

Purity by HPLC (%): 99.61

Impurity-1(%): 0.12

Impurity-2(%): ND

Impurity-3(%): 0.12

Impurity-4(%): ND

Diastereomers (%)

Diastereomer-1: 48.17

Diastereomer-2: 51.83

XRD (°2Theta; Cu): Halo at 26

DSC (30°-300° C.) At 10° C./min: 159.4° C. (endotherm)

Example-13

To aqueous sodium hydroxide (1.82 g sodium hydroxide in 120 mL demineralized water) and methanol (240 mL), cooled to 15-20° C., 10-Propargyl-10-deazaminopterin dimethyl ester (10.0 g) was added and stirred the reaction mass till the completion of reaction which was monitored by HPLC. pH of the reaction mass was adjusted with acetic acid (0.90 mL) at 15-20° C. The volume of reaction mixture was reduced to 100-120 mL by recovering the solvent(s) under vacuum below 45° C. demineralized water (350 mL) was added to the residual solution at 20-30° C. Aqueous acetic acid (4.75 mL of acetic acid in 50 mL demineralized water) was added slowly at 20-30° C. over a period of 30-40 min. The reaction mass was stirred for 25-30 minutes at 20-30° C. and the slurry obtained was filtered under vacuum, washed with demineralized water (3×50 mL) and suck-dried for 1-2 hours and then dried under vacuum at 50-55° C. for 12-16 hrs. To the vacuum dried product 10% methanol in dichloromethane (7 mL of methanol in 63 mL dichloromethane) was added at 20-30° C. accompanied by stirring for 2-3 hrs. The Solid was filtered, washed with 10% methanol in dichloromethane (2 mL of methanol in 18 mL dichloromethane) and suck-dried for 1-2 hrs. The suck-dried solid was stirred with demineralized water (100 mL) at 20-30° C. for 25-30 min, filtered, washed with demineralized water (3×50 mL), suck-dried for 2-3 hrs followed by washing with chilled (0-5° C.) acetone (2×50 mL), suck-dried for 1-2 hrs and then dried under vacuum at 50-55° C. till water content is less than 4.5% w/w.

Weight (g): 7.6
Yield (%): 80.8
Water content (% w/w): 1.7
Purity by HPLC (%): 99.63
Impurity-1(%): 0.04
Impurity-2(%): 0.02
Impurity-3(%): 0.07
Impurity-4(%): 0.09
Diastereomers (%)
Diastereomer-1: 50.08
Diastereomer-2: 49.92
XRD (°2Theta; Cu): 8.57, 10.82, 12.29, 14.23, 14.92, 15.83, 18.96, 21.81, 24.20, 24.78, 27.53, 28.97, 30.17, 34.20
DSC (30°-300° C.) At 10° C./min: 224.6° C. (endotherm)

Example-14

To aqueous sodium hydroxide (1.82 g sodium hydroxide in 120 mL demineralized water) and methanol (240 mL), cooled to 15-20° C., 10-Propargyl-10-deazaminopterin dimethyl ester (10.0 g) was added and stirred the reaction mass till the completion of reaction which was monitored by HPLC. pH of the reaction mass was adjusted with acetic acid (0.90 mL) at 15-20° C. The volume of reaction mixture was reduced to 100-120 mL by recovering the solvent(s) under vacuum below 45° C. demineralized water (350 mL) was added to the residual solution at 20-30° C. Aqueous acetic acid (4.75 mL of acetic acid in 50 mL demineralized water) was added slowly at 20-30° C. over a period of 30-40 min. The reaction mass was stirred for 25-30 minutes at 20-30° C. and the slurry obtained was filtered under vacuum, washed with demineralized water (3×50 mL) and suck-dried for 1-2 hours and then dried under vacuum at 50-55° C. for 12-16 hrs. To the vacuum dried product 10% methanol in dichloromethane (7 mL of methanol in 63 mL dichloromethane) was added at 20-30° C. accompanied by stirring for 2-3 hrs. The Solid was filtered, washed with 10% methanol in dichloromethane (2 mL of methanol in 18 mL dichloromethane) and suck-dried for 1-2 hrs. The suck-dried solid was stirred with demineralized water (100 mL) at 20-30° C. for 25-30 min, filtered, washed with demineralized water (3×50 mL), suck-dried for 2-3 hrs followed by washing with chilled (0-5° C.) acetone (2×50 mL), suck-dried for 1-2 hrs and then dried under vacuum at 50-55° C. till water content is less than 4.5% w/w.

Weight (g): 7.5
Yield (%): 79.7
Water content (% w/w): 1.7
Purity by HPLC (%): 99.60
Impurity-1(%): 0.04
Impurity-2(%): 0.02
Impurity-3(%): 0.06
Impurity-4(%): 0.08
Diastereomers (%)
Diastereomer-1: 50.26
Diastereomer-2: 49.74
XRD (°2Theta; Cu): 8.51, 10.82, 12.28, 14.29, 14.99, 15.81, 18.97, 21.86, 24.17, 24.82, 27.58, 29.00, 30.24, 34.14
DSC (30°-300° C.) At 10° C./min: 224.1° C. (endotherm)

Example-15

To Pralatrexate (100 mg; 99.47% Purity; Diastereomer 1—50.25, Diastereomer 2—49.75) 50% methanol in dichloromethane (1.5 mL of methanol in 1.5 mL dichloromethane) was added at 20-25° C. and stirred for 2 hrs. The solid was filtered and washed with 50% methanol in dichloromethane (0.25 mL of methanol in 0.25 mL dichloromethane). The product was dried under vacuum at 50-55° C. for 12-14 hrs.

Weight (g): 0.057
Yield (%): 57
Purity by HPLC (%): 99.65
Diastereomers (%)
Diastereomer-1: 46.85
Diastereomer-2: 53.15

Example-16

To Pralatrexate (500 mg; 99.66% Purity; Diastereomer 1—50.09, Diastereomer 2—49.91) 25% methanol in dichloromethaneE (3.5 mL) was added at 20-30° C. and stirred for 3-4 hrs. The solid was filtered, washed with 25% methanol in dichloromethane (1.0 mL), suck-dried for 1-2 hrs, followed by drying under vacuum at 50-55° C. for 16 hrs.

Weight (g): 0.410
Yield (%): 82
Purity by HPLC (%): 99.73
Diastereomers (%)
Diastereomer-1: 49.91
Diastereomer-2: 50.09

Example-17

To Pralatrexate (500 mg; 99.66% Purity; Diastereomer 1—50.09, Diastereomer 2—49.91) 10% methanol in dichloromethaneE (3.5 mL) was added at 20-30° C. and stirred for 3-4 hrs. The solid was filtered, washed with 10% methanol in dichloromethane (1.0 mL), suck-dried for 1-2 hrs, followed by drying under vacuum at 50-55° C. for 16 hrs.

Weight of dry PRA-6 (g): 0.425
Yield (%): 85
Purity by HPLC (%): 99.74
Diastereomers (%)
Diastereomer-1: 49.94
Diastereomer-2: 50.06

The invention claimed is:

1. A process for the preparation of pralatrexate of Formula (I), the method comprising the steps of:

a) alkylating a compound of Formula (II)

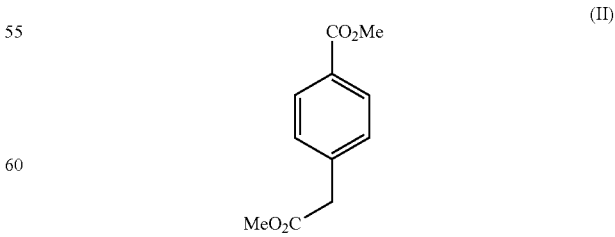

with an alkylating agent in the presence of a suitable base and phase transfer catalyst to obtain a compound of Formula (III);

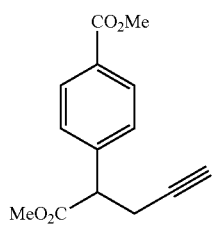

b) coupling the compound of Formula (III) obtained in step (a) with a compound of Formula (IV) or its acid addition salt in the presence of a base and a suitable solvent

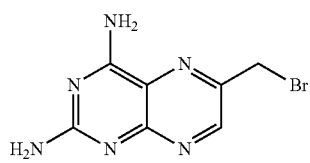

to obtain a compound, which is treated with an acid to give a compound of Formula (V),

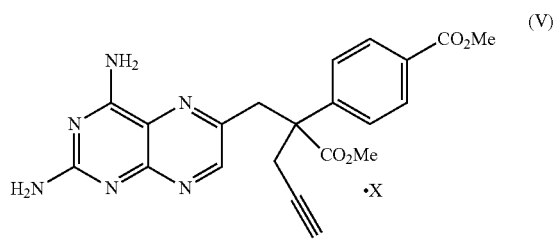

wherein X is an acid;

c) treating the compound of Formula (V) with a suitable base to give a compound of Formula (VI);

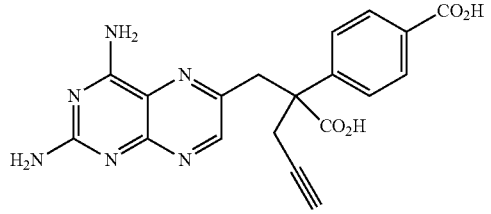

d) optionally converting the compound of Formula (VI) to a compound of Formula (VII), by treatment with a suitable base,

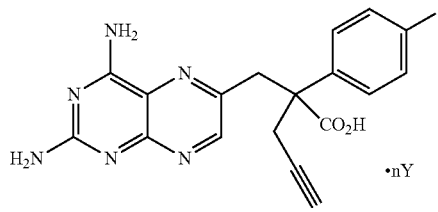

wherein Y is a base, and n is 1 or 2;

e) decarboxylating the compound of Formula (VI) or the compound of formula (VII) by heating in a suitable solvent to obtain a compound, which is treated with a base to give a compound of Formula (VIII),

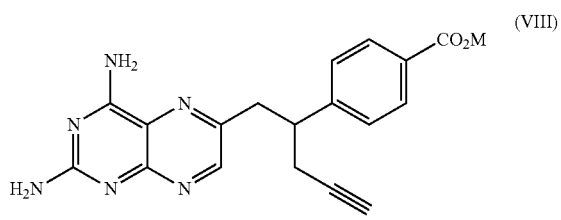

wherein M is an alkali metal;

f) optionally purifying the compound of Formula (VIII) with a suitable solvent or a mixture of solvents;

g) coupling the compound of Formula (VIII) obtained in step (f) with a compound of Formula (IX)

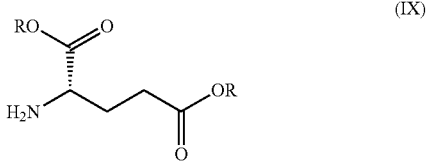

in the presence of a suitable dehydrating agent and an activating agent, wherein R is a C1-C4 alkyl group, to give a compound of Formula (X),

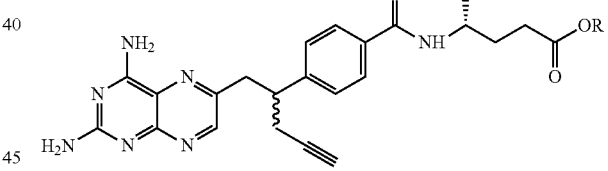

wherein R is as defined herein above; and h) hydrolysing the compound of Formula (X) obtained in step (g) in presence of a suitable base to give a compound of Formula (I)

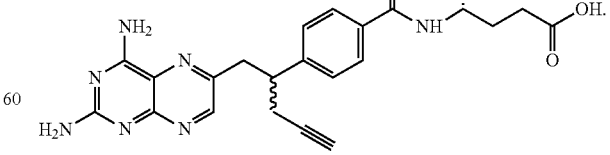

2. The process of claim 1, wherein the alkylating agent of step (a) is propargyl bromide.

3. The process of claim 1, wherein the base of step (a) is potassium carbonate.

4. The process of claim 1, wherein the phase transfer catalyst of step (a) is tetra butyl ammonium iodide.

5. The process of claim 1, wherein the base of step (b) is sodium hydride.

6. The process of claim 1, wherein the suitable solvent of step (b) is dimethylacetamide.

7. The process of claim 1, wherein the acid of step (b) is HCl or HBr.

8. The process of claim 1, wherein the base of step (c) is potassium hydroxide.

9. The process of claim 1, wherein the base of step (d) is dicyclohexylamine and n is 2.

10. The process of claim 1, wherein the suitable solvent of step (e) is dimethylacetamide or dimethylsulfoxide.

11. The process of claim 1, wherein the suitable base of step (e) is sodium hydroxide.

12. The process of claim 1, wherein the activating agent of step (g) is 1-hydroxybenztriazole.

13. The process of claim 1, wherein the suitable dehydrating agent of step (g) is 1-(3-dimethyl-aminopropyl)-3-ethylcarbodiimide hydrochloride.

14. The process of claim 1, wherein the suitable base of step (h) is sodium hydroxide.

15. A compound of Formula (V),

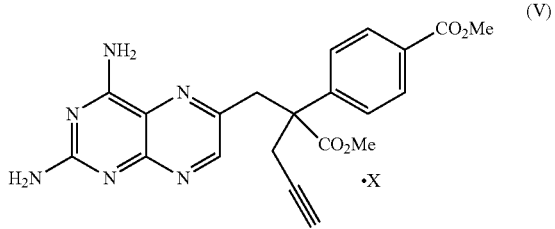

wherein X is HCl or HBr.

16. The compound of claim 15, wherein X is HBr.

17. A compound of Formula (VII),

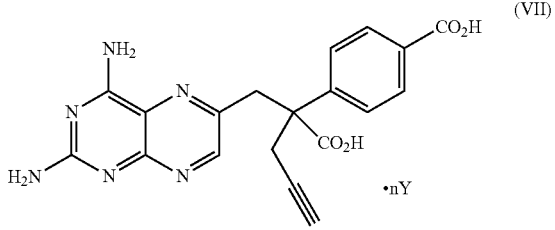

wherein Y is a base selected from the group consisting of dicyclohexylamine, ammonia, alkylamines, benzathine, hydrabamine, arginine, lysine, N,N'-dibenzylethylene-diamine, chloroprocaine, choline, diethanolamine, ethylenediamine, N-methyl-glucamine, 1,5-diazabicyclo[5.4.0]undecene, piperidine, ethanolamine, pyrrolidine, morpholine, piperazine, cyclohexaneamine, and procaine, and n is 1 or 2.

18. The compound of claim 17, wherein Y is dicyclohexylamine and n is 2.

19. A compound of Formula (VIII),

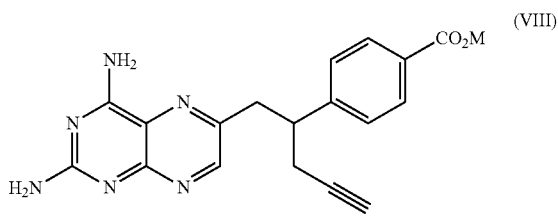

wherein M is an alkali metal.

20. The compound of claim 19, wherein M is sodium, lithium or potassium.

21. A process for obtaining substantially pure pralatrexate of Formula (I)

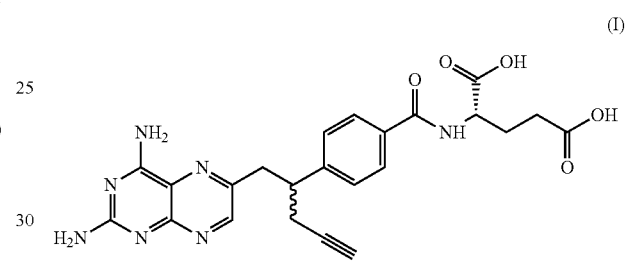

comprising the steps of
a) contacting pralatrexate with a mixture of alcohol and halogenated hydrocarbon to obtain a first mixture;
b) stirring the first mixture at ambient temperature;
c) collecting a solid from the first mixture;
d) contacting the solid of step (c) with demineralized water to obtain a second mixture;
e) stirring the second mixture of step (d) at ambient temperature; and
f) isolating the substantially pure pralatrexate, wherein the content of each diastereomer at C10 position is 50±0.6% and the substantially pure pralatrexate has a high performance liquid chromatography (HPLC) purity of not less than 99.5%.

22. The process of claim 21, wherein the mixture of alcohol and halogenated hydrocarbon of step a) has a volume ratio of about 1:9.

23. The process of claim 21, wherein the alcohol of step a) is methanol.

24. The process of claim 21, wherein the halogenated hydrocarbon of step a) is dichloromethane.

25. The process of claim 21, wherein the ambient temperature of step b) and the ambient temperature of step e) is 15 to 30° C.

* * * * *